Figure 1:
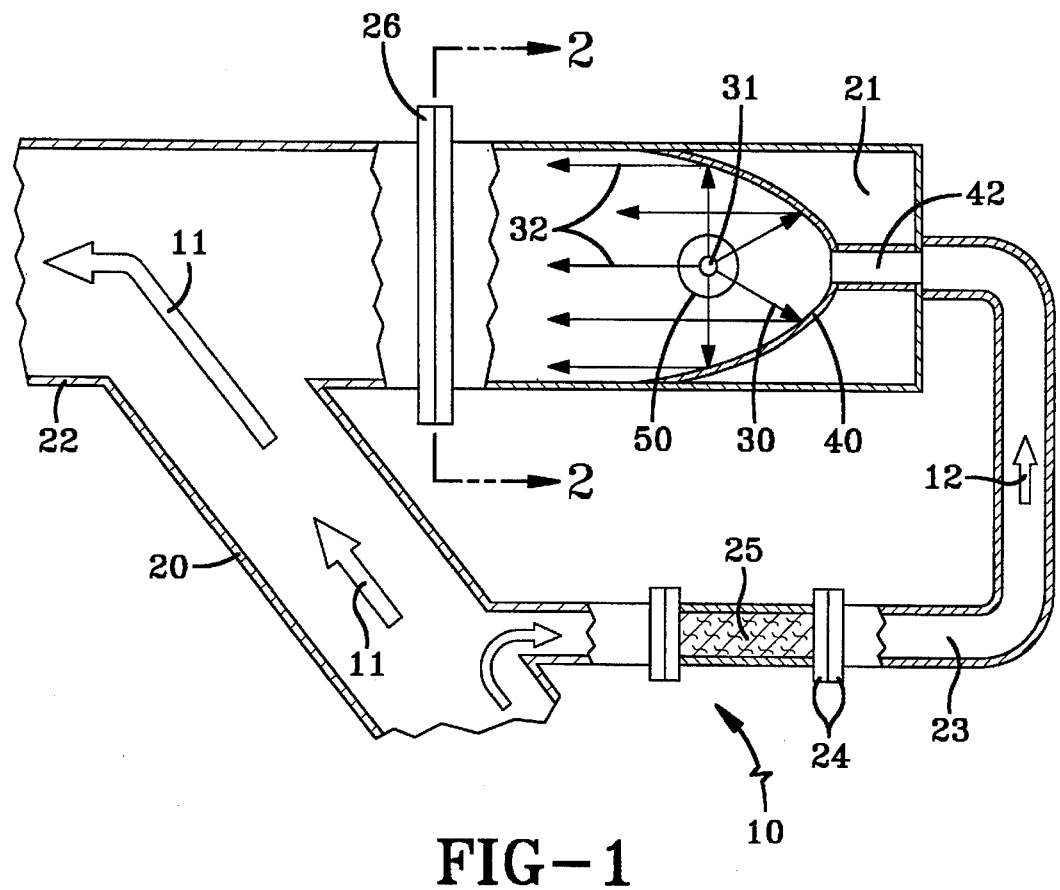
Figure 2:
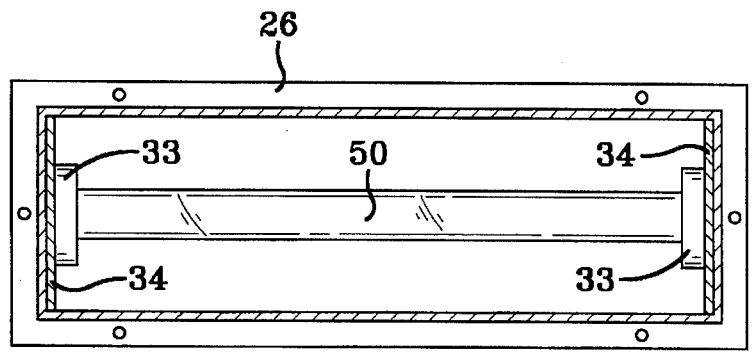

United States Patent [19]
Glazman

[11] Patent Number: 5,635,133
[45] Date of Patent: Jun. 3, 1997

[54] METHOD AND APPARATUS FOR KILLING MICROORGANISMS IN A FLUID MEDIUM

[76] Inventor: Mark Glazman, 2725 Floribunda Dr., Columbus, Ohio 43209

[21] Appl. No.: 521,527

[22] Filed: Aug. 30, 1995

[51] Int. Cl.[6] .................................................. A61L 2/10
[52] U.S. Cl. .................. 422/24; 250/432 R; 250/436; 250/438; 422/121
[58] Field of Search .................... 422/24, 186.3, 422/905, 121; 55/279; 250/432 R, 436, 438; 210/748

[56] References Cited

U.S. PATENT DOCUMENTS

| | | | |
|---|---|---|---|
| 3,105,733 | 10/1963 | Potapenko | 422/121 |
| 4,116,630 | 9/1978 | Meacham, Jr. et al. | 422/24 |
| 4,141,830 | 2/1979 | Last | 422/24 |
| 4,948,980 | 8/1990 | Wedekamp | 250/432 R |
| 5,112,370 | 5/1992 | Gazzano | 422/121 |
| 5,200,156 | 4/1993 | Wedekamp | 422/24 |
| 5,330,722 | 7/1994 | Pick et al. | 422/121 |

OTHER PUBLICATIONS

Riley, "Ultra Violet Air Disinfection for Control of Respiratory Contagion", *Architectural Design & Indoor Microbial Pollution*, pp. 174–197.

Westinghouse, "Sterilamp".

"Sterile Air–Conditioning Ultraviolet Systems", American Ultraviolet Company, 1976.

*Primary Examiner*—Timothy McMahon

[57] ABSTRACT

A method and apparatus (10) for killing microorganisms in a particle laden fluid medium (11) are disclosed. This method has the steps of providing a germicidal radiation for killing microorganisms (30) and a reflectors (40) for transferring and orienting of the germicidal radiation for killing microorganisms (30); providing a secondary flow (12) of a substantially particles free fluid; the secondary flow (12) is running along or flowing across the surface of the reflectors (40) and establishing a substantially particle free barrier environment maintaining clean the reflectors (40); orienting an emission of the germicidal radiation in a parallel array of beams (32), and passing the fluid medium (11) along a path aligned with the parallel array of beams (32). The apparatus arranged so that the maximum efficiency of use of germicidal energy is achieved, energy consumption for sterilization will decrease, reliability and period between maintenance will increase.

18 Claims, 2 Drawing Sheets

METHOD AND APPARATUS FOR KILLING MICROORGANISMS IN A FLUID MEDIUM

FIELD OF THE INVENTION

The present invention relates to fluid purification and in particular sterilization by irradiation with an ultraviolet radiation source.

BACKGROUND OF THE INVENTION

The airborne transmission of bacteria and viruses, chiefly respiratory disease organisms is a serious problem in health care. The control of airborne disease transmission has become increasingly important with an increasing number of people growing older with weakened immune systems more vulnerable to airborne disease or infected with human immunodeficiency virus (HIV) or other airborne and difficult to cure diseases. This coupled with antibiotic resistant strains of bacteria have created a need for inexpensive, efficient air purification systems. The spread of air born infections can be reduced by killing the infectious microorganism by ultraviolet (UV) radiation. Ultraviolet radiation to destroy airborne microorganisms can be used in ceiling fixtures suspended above the people in the room or inside ventilation system air duct. The continuing spread of tuberculosis (TB) infection and other airborne disease in modern health institutions, correctional institutions, and shelters for homeless indicates however, that the known air purification systems are inadequate in controlling the spread of airborne microorganisms.

An other important field where the spread of microorganisms needs to be controlled is liquid, and particularly water-based solutions.

The sterilization by ultraviolet radiation has been known more than fifty years. Various methods and apparatus have been invented for ultraviolet irradiating fluids, air and water in particular, in order to control the spread of microorganisms by destroying those microorganisms with a sufficient dose of radiation.

Air purification by means of filtration and irradiation is widely practiced. Conventional air cleaning systems commonly have a filtration and in irradiation units. Irradiation is placed after filtration because the ultraviolet lamps used as a source of the radiation readily attract dust which can accumulate on a surface of the lamp, block the UV radiation inside the lamp and interfere with their germicidal effect.

Commonly irradiation is placed before humidification because ultraviolet radiation is most effective in an atmosphere with relative humidity less than 70% which promotes oxidation. Ultraviolet germicidal radiation has been proven to be more effective and economically feasible than any other approach to reducing the number of microorganisms in the liquid or gas flow. Conventional UV fluid sterilization systems have relied on exposure of suspended microorganisms to ultraviolet radiation by passing medium over or around one or more ultraviolet lamps. This method is used in U.S. Pat. Nos. 5,112,370 and 5,200,156. This method has a number of shortcomings.

The first shortcoming of the previous art is their low reliability. The particles suspended in the fluid accumulate on the surface of the lamp or protective tubes, forming the UV light absorption layer, which restricts or eliminates the germicidal effectiveness. The reliability and actual germicidal effectiveness depend on the quality of the medium filtration and come very small and unpredicted if the medium is unfiltered or poorly filtered.

The second shortcoming of previous art of UV sterilization systems is that they have low efficiency of use of the UV energy, because their lamps accumulate particles on the surface from the beginning and because in ducts or pipes with ratio length-L to diameter-D L/D=10:1 only 6% of beams have their path the length equal to the longest available way (L/2 that is when the lamp is placed halfway between the longest straight line length of the duct (L), the maximum available way is only L/2), other beams 94% are directed on paths much shorter and could irradiate smaller volume on its wax, and hence less efficient.

The third shortcoming of previous art is nonuniform irradiation intensity in an irradiated volume. In the device for sterilization according to U.S. Pat. No. 5,200,156 the author tried to achieve more uniform irradiation intensity than before by applying a flat oval cross section fight source with or without the reflectors. But this invention made limited progress because the device according to the U.S. Pat. No. 5,200,156 can irradiate towards axis of pipe only 50% of radiation and only 6% of the beams will have length equal to the length of the longest available way. Other beams are short slanting beams. They irradiate smaller volume than longest beams and are absorbed by the pipe walls. Due to the early absorption, the efficiency of the use of short slanting beams is very low. As a result the efficiency of all previous art, including the sterilizer according to U.S. Pat. No. 5,200,156 is too low.

The fourth shortcoming of previous art according to U.S. Pat. No. 5,200,156 is that the sources of radiation are installed inside the medium flow, liquid or gas, and create a substantial pressure loss in the system. To retrofit an operating ventilation or other system with known UV sterilization system it is necessary to replace a fan, pump, electric motor by more powerful ones. As a result capital and operating expenses would increase.

The prior art therefore suffers from number of disadvantages which can be improved upon.

SUMMARY OF THE INVENTION

It is an object of the present invention to provide a method for killing microorganism in a flowing fluid medium using germicidal beams as a means for killing the microorganisms in a straight portion of the flow path, the method has the steps of:

providing a primary flow of fluid medium containing particles and microorganisms providing a plurality means for killing microorganisms, the means being immersed in the fluid medium containing particles and microorganisms; providing a means for a transferring of the means for killing of microorganisms, at least one of the means for transferring being immersed in the fluid medium;

providing a secondary flow of substantially particle free fluid, the secondary flow is running along or flowing across the surface of the means for transferring which is immersed in said fluid medium and establishing a substantially particulate free barrier environment maintaining the immersed means for transferring clean;

providing a means for orientating of the means for killing microorganisms, the means for orientating is orientating the means for killing in an array of substantially parallel germicidal beams aligned along the straight portion of flow path; providing a means for means for energizing of the means for killing microorganisms and energizing the means for killing microorganisms.

The advantage of the present invention is the provision of the secondary flow that runs along the surfaces immersed in the fluid means for transferring and prevents accumulation on the surfaces the particles suspended in the fluid medium. This advantage makes the reliability of the method and apparatus according to the present invention high and predictable.

It is a further object of invention to provide filtering of the secondary flow.

It is a further object of invention to energize the means for killing microorganisms, by the means for energizing, having one or more arcs of a ultraviolet lamps. The arcs of ultraviolet lamps emit the means for killing microorganisms, which is an emission of ultraviolet germicidal beams.

It is a further object of invention to orient the emission of the ultraviolet beams into a substantially parallel array of beams and to pass the fluid medium along a straight portion of the flow path aligned with the array of parallel ultraviolet beams, the straight portion of the flow path being of sufficient length to allow the array of ultraviolet beams to kill microorganisms. An other advantages of the present invention is the maximum uniformity of the irradiation intensity in an irradiated volume, because the beams were oriented in a substantially parallel array, which is parallel the fluid flow and will not suffer from early absorption by walls. The efficiency of use of ultraviolet energy of the ultraviolet lamps will reach the maximum because according to the present invention the maximum amount of UV beams was oriented parallel and because they have the length equal to the longest available wave.

According to the preferred embodiment of the invention a substantially parabolic reflector is provided around each the ultraviolet lamp. The arc of the lamp is situated in the focus of the reflector. As a result the maximum amount of the ultraviolet lamp emission is oriented in the parallel array of beams. According to the other preferred embodiment, each of the reflectors is provided with an aperture for accepting at least a portion of the secondary flow of substantially particulate free fluid; and passing the portion of the secondary flow of fluid through each the reflector. As a result, the surfaces of the reflector and the lamp will remain clean and provide maximum transfer of radiation to the fluid medium.

According to an other preferred embodiment a fluid impenetrable wall is provided as a means for transferring which can allow the irradiation for the means for killing microorganisms to pass or be transmitted. The wall imperviously separates the fluid medium from the means for orienting and the means for energizing. This embodiment could be applied when the fluid medium is liquid or gas. The additional advantage of this embodiment is a safe and convenient maintenance of the lamps and reflectors because they are located outside of the fluid medium.

It is a further object of invention to provide an apparatus for killing microorganisms in the fluid medium, the apparatus having: the fluid medium; the means for passing the fluid medium; the means for killing microorganisms; a means for transferring of the means for killing of microorganisms in the fluid medium, at least one of the means for transferring been immersed in the fluid medium; a means of energizing the means for killing microorganisms; a means for passing a secondary flow of fluid medium, the secondary flow being substantially particles free, the secondary flow running along or flowing across the means for transferring and establishing a substantially particulate free barrier environment maintaining clean the means for transferring.

Preferably the means for passing the secondary flow of the fluid medium has a filter, the filter being sufficient to remove particles from the secondary flow. The secondary flow is a small part of the fluid medium and the filter to remove particles the secondary flow is also small and inexpensive. The flow through the filter is very small and has the velocity 0.1–0.25 m/sec, (20–50 FPM) and its life time is a few times longer than the life time of a filter which conventionally is used for the filtration of the prime flow with the velocity 1.27 m/sec(250 FPM). As a result the means for transfer remain clean independently of the purity of the fluid medium, the period between the maintenances is much longer, and the reliability of the apparatus is higher than previously known arts.

Preferably the means for energizing has one or more arcs of ultraviolet lamps for emitting ultraviolet beams. The lamps emit an ultraviolet radiation in the medium and are well known as the most effective source of germicidal radiation.

Preferably the means for transferring further has a means for orienting the emission of the ultraviolet beams into a substantially parallel array of beams. The substantially parallel array of the beams provides most effective use of the ultraviolet energy. Preferably the means of orienting the ultraviolet beams is a substantially parabolic reflector with the arc of ultraviolet lamp situated in its focus.

Preferably a means for passing the fluid medium along a path aligned with the array of parallel ultraviolet beams is provided, the path being of sufficient length to allow the array of beams of ultraviolet radiation to kill microorganisms.

Preferably the means for passing the fluid medium is a straight prime conduit. The means of orienting is situated at the end of the straight prime conduit and is faced at the prime conduit.

According to preferred embodiment the substantially parabolic reflector having an aperture open to the secondary flow is used as the means for orienting. The substantially parabolic reflector preferably is open to the prime conduit at a first end, at a second end, the substantially parabolic reflector is open for passing of the secondary flow of the fluid medium. The secondary flow is running along the substantially parabolic reflector and the lamp located in the reflector cavity and establishing a substantially particulate free barrier environment maintaining the surfaces of the substantially parabolic reflector and lamp clean.

The advantages of the invention can be seen in Table 1 as a result of a comparison of the units for air sterilization in the ducts 0.89 m×1.02 m×2.54 m (35"×40"×100") with airflow 50.67 m3/sec (10000 CFM), temperature 26.6° C. (80° F). The source of germicidal radiation is the germicidal lamps G36T6H with ultraviolet output 13.8 W per lamp. Unit 1 is a unit according to the previous art with two rows of the lamps installed across to the air flow. Unit 2 is the unit according to this invention. The relative air-flow resistance is the ratio between the coefficient of pressure losses in the unit 1 and the coefficient of pressure losses I and 2. Relative efficiency is the ratio between the efficiency of the unit at present time and the efficiency of the unit at the initial moment of operation. The efficiency is defined from the equation N/No where No is the number of microorganisms in the medium before the treatment and N is the number of inactivated microorganisms in the media after the treatment. The units are the percentage.

TABLE 1

| Number of the Unit | Number of the lamps in the unit | Size of the unit, inches | Wattage of the unit UV, Watt | Relative air flow resistance | Relative efficiency at the beginning of the operation | Relative efficiency after one month of the operation |
| --- | --- | --- | --- | --- | --- | --- |
| 1 | 47 | 35 × 40 × 36 | 662 | 47 | 100 | 20 |
| 2 | 16 | 35 × 40 × 16 | 226 | 1 | 100 | 100 |

The unit 2 is estimated to be about five times more efficient after one month of operation, uses three limes less ultraviolet lamps and energy, and has very low air flow resistance.

Figure 3:
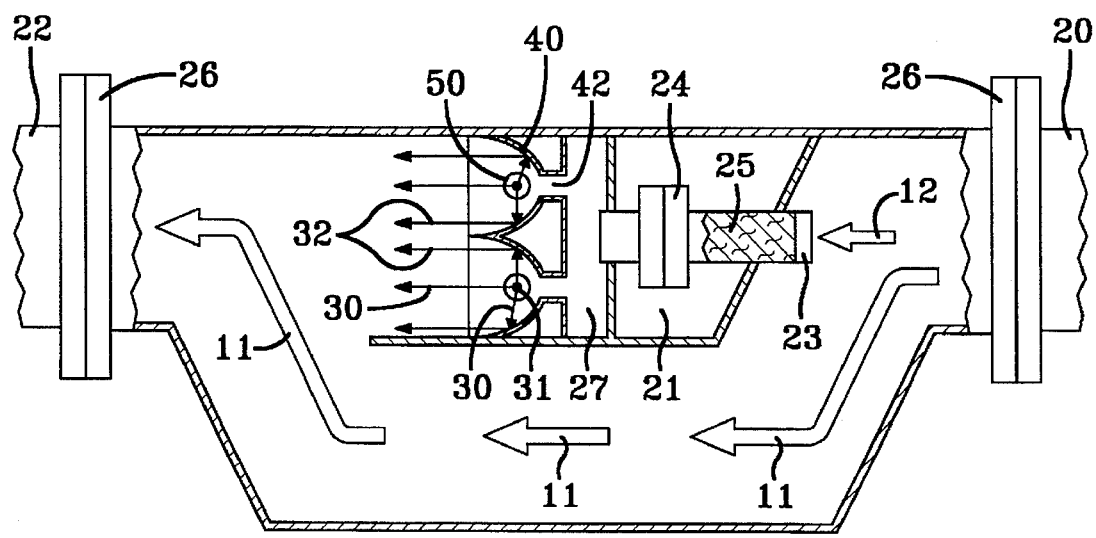

According to another preferred embodiment, the means for transferring have a fluid impenetrable, germicidal radiative transmissible wall, imperviously covering the end of the straight prime conduit, wherein the means for killing of microorganisms enter in and separated the fluid flow from means for orienting and means for energizing. The fluid impenetrable wall separates the compartment, wherein the substantially parabolic reflector and lamp are located. This embodiment could be preferable when the fluid is liquid or when fluid flow has to be separated from the means of energizing and the means of orienting. The advantages of the present invention is the provision of the location of means for energizing and means for transferring outside of the fluid flow that is providing the convenience and safe maintenance of a electrical contacts of the lamps and surfaces of the lamps and reflectors.

BRIEF DESCRIPTION OF THE DRAWINGS

The invention will now be explained by way of example only and with reference to the following drawings wherein:

FIG. 1 is a schematic view of a first preferred embodiment of the invention showing an apparatus for killing microorganisms in a fluid medium with a vertical cross-sectional view taken along axis of the means for passing the fluid medium to expose the components of the apparatus for killing microorganisms;

FIG. 2 is a vertical cross-sectional view taken along lines 1—1 of the apparatus for killing microorganisms shown in FIG. 1, illustrating the means for transferring and means for energizing components of the apparatus for killing microorganisms;

FIG. 3 is a schematic view of a second preferred embodiment of the invention showing the apparatus for killing microorganisms with two lamp light source;

FIG. 4 is a schematic view of the third preferred embodiment showing the apparatus for killing microorganisms with a separated radiative compartment.

DETAILED DESCRIPTION OF THE PREFERRED EMBODIMENT

The present invention provides the apparatus for killing microorganisms, generally referred to by reference 10. First preferred embodiment of the invention is shown in FIG. 1 and FIG. 2. The means for passing the fluid medium is conduit 20, having the straight prime conduit 22. The beginning portion of the straight prime conduit 22 is connected with dead end chamber 21, by flanges 26. The dead end chamber 21 is open towards the flow of the fluid medium 11, and faces towards the straight prime conduit 22.

The means for transferring are the parabolic reflector 40 and the envelope 50 of the ultraviolet lamp. In addition to that parabolic reflector 40 is the means for orienting. The means for energizing is an arc 31 of the ultraviolet lamp enclosed in a transparent for ultraviolet radiation envelope 50. The parabolic reflector 40 is located inside dead end chamber 21. The arc 31 of the ultraviolet lamp is situated in the focus of the parabolic reflector 40 by the lampholders 33. The lampholders 33 are mounted on the side panels 34. The parabolic reflector 40 is installed such that its axis or axis plane is parallel to the axis or axis plane of the straight prime conduit 22. The parabolic reflector 40 has an aperture 42.

According to the first preferred embodiment, the means for passing the secondary flow include a secondary conduit 23 with a filter 25 installed by flanges 24. The intake end of the secondary conduit 23 is connected and open to the means for passing of the fluid medium 20. The outlet of the secondary conduit is connected with the dead end chamber 21. The filter 25 is an effective particulate filter. In case of the air filtration the high efficiency particulate filters or electrostatic filter could be used but the application of other filters is not limited.

According to the first preferred embodiment, the method and apparatus for killing microorganisms in the fluid media is realized as follows:

The fluid medium 11 is coming through the means for passing the fluid medium, conduit 20 and entering in the straight prime conduit 22. The secondary flow medium 12 is a small part of the fluid medium 11 and goes through the means for passing the secondary flow, conduit 23 including the effective particulate filter 25. The filter 25 captures and arrests the particles suspended in the secondary flow medium 12. The clean secondary flow medium comes in the end of the chamber 21 and through the aperture 23 comtacts the reflector 40 and the lamp envelope 50, fills up the cavity of the reflector 40 and protects the lamp envelope 50 and the reflector 40 from the accumulation of the particles from the flow of the fluid medium 11.

At the same time the arc of the ultraviolet germicidal lamp 31 emits the means for killing microorganisms the means being germicidal beams 30. The means for transferring, the lamp envelope 50 transfers the germicidal beams 30 to the other means for transferring, the parabolic reflector 40. Due to the parabolic shape and the situation of the arc 31 in the focus of the parabolic reflector 40, the parabolic reflector is the means for orientation. The parabolic reflector orients the germicidal beams 30 into a substantially parallel array of ultraviolet beams 32. The straight prime conduit 22 pass the fluid medium 11 along a path aligned with the array of the substantially parallel ultraviolet beams 32.

The substantially parallel array of the ultraviolet beams maximizes and uniformly radiates the fluid 11 passing the straight prime conduit 22. The microorganisms suspended in the fluid absorb the substantially parallel arrays of beams 32, are killed before passing the end of the straight prime conduit 22.

The second preferred embodiment is shown in FIG. 3. The apparatus 10 has the dead end chamber 21, which is installed inside the flow of the fluid medium 11. The dead end chamber 21 contains two parabolic reflectors 40, the germicidal lamps with arcs 31 situated in focuses of the reflectors 40, a receiver 27 and the means for passing the secondary flow 23. The number of lamps and reflectors 40 is not limited to two. If it is necessary a larger number of reflectors 40 could be situated in the dead end chamber 21. The fluid medium 11 flows in the apparatus for killing microorganisms 10, runs along outside the dead end chamber 21 and continues to move along the straight prime conduit 22. The secondary flow medium 12 is a small part of the fluid medium 11 and goes through the effective particulate filter 25. The filter 25 captures and arrests particles suspended in the secondary flow medium 12. Clean secondary flow medium comes in the receiver 27. The receiver 27 is a chamber with impenetrable walls having input to the clean secondary flow of the fluid medium and output connected with the apertures 42 of the parabolic reflectors 40. The clean medium comes through the aperture 42 fills up the cavity of the reflector 40 and protects the lamp envelopes 50 and the reflectors 40 from accumulation of the particles from the fluid medium 11.

At the same time the arcs of the ultraviolet germicidal lamps 31 emit the germicidal beams 30. The means for transferring, the lamp envelops 50 transfers the germicidal beams 30 to the other means for transferring, the parabolic reflectors 40. Each parabolic reflector 40 orients the germicidal beams 30 in the substantially parallel array of the ultraviolet beams 32. The straight prime conduit 22 passes the fluid medium 11 along a path aligned with the array of the substantially parallel ultraviolet beams 32.

The substantially parallel array of the ultraviolet beams 32 maximizes and uniformly radiates the fluid 11 passing through the straight prime conduit 22. The microorganisms suspended in the fluid absorb the substantially parallel arrays of beams, and are killed in the straight prime conduit 22.

Figure 4:
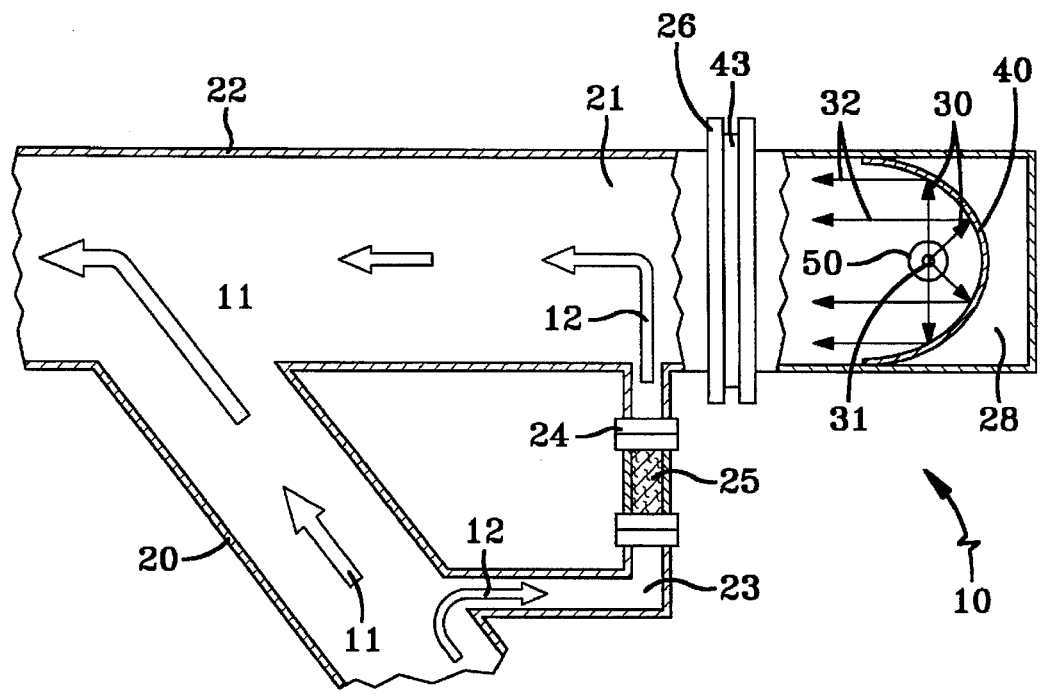

The third preferred embodiment is shown on FIG. 4 and includes the means for passing the fluid medium, conduit 20, having the straight prime conduit 22. The beginning of the straight prime conduit 22 is connected with the dead end chamber 21. The dead end chamber 21 opens towards the flow of the fluid medium 11, and faces towards the straight prime conduit 22. At the closed end of the dead end chamber 21 is a transmissible wall 43, transferring the means for killing and impenetrable for the fluid medium 11. The transmissible wall 43 separates the fluid medium 11 from the parabolic reflectors 40, lamp envelopes 50 and electrical connectors located in the radiative chamber 28.

The means for transferring are the parabolic reflector 40 and the envelope 50 of the ultraviolet lamp. In addition to that parabolic reflector 40 is the means for orienting. The means for energizing is the arc 31 of the ultraviolet lamp enclosed in a transparent for ultraviolet radiation envelope 50. The parabolic reflector 40 is located inside the radiative chamber 28. The arc 31 of the ultraviolet lamp is situated in the focus of the parabolic reflector 40. The parabolic reflector 40 is installed such that its axis or axis plane is parallel to the axis or axis plane of the straight prime conduit 22.

According to the third preferred embodiment the means for passing the secondary flow include a secondary conduit 23 and a filter 25 installed by flanges 24. The intake end of the secondary conduit 23 connected and open to the means for passing of the fluid medium 20. The outlet of the secondary conduit is connected with the dead end chamber 21. The filter 25 is effective particular filter. The filter 25 captures and arrests particles suspended in the secondary flow medium 12. Clean secondary flow medium coming in the dead end chamber 21 and through the aperture 41 runs along the transmissible wall 43, fills up the dead end chamber 21 and protects the transmissible wall 43 from accumulation of the particles from the flow of the fluid medium 11.

At the same time the arc 31 of the ultraviolet germicidal lamp emits the germicidal beams 30. The means for transferring, the lamp envelopes 50 transfers the germicidal beams 30 to the other means for transferring, the parabolic reflectors 40. The parabolic reflector orients germicidal beams 30 in the substantially parallel array of the ultraviolet beams 32. The straight prime conduit 22 passes the fluid medium 11 along a path aligned with the array of the substantially parallel ultraviolet beams 32.

The substantially parallel array of the ultraviolet beams 32 pass through the transmissible wall 43, maximizing and uniformly radiating the fluid 11 passing the straight prime conduit 22. The microorganisms suspended in the fluid absorb the substantially parallel arrays of beams are killed prior to passing the end of the straight prime conduit 22. For additional increasing of efficiency in an outlet end of the straight prime conduit 22 a flat reflector could be installed. The flat reflector should also be maintained clean by a secondary flow of substantially particles free fluid 11 as described above; the secondary flow running along or flowing over the surface of the reflector, creating a barrier of a particle free media or flow.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

We claim:

1. A method for killing microorganisms in a flowing fluid medium using germicidal beams as a means for killing the microorganisms in a straight portion of the flow path, the method comprising of steps of:

providing a primary flow of a fluid medium containing particles and microorganisms;

providing a means for killing microorganisms, the means being an emission of germicidal beams, said means being immersed in said fluid medium containing particles and microorganisms along a straight portion of the flow path;

providing a plurality of means for transferring the emission of germicidal beams, at least one of the means for transferring being a means for transferring and orienting the emission of the germicidal beams; the means for transferring and orienting orients the emission of the germicidal beams into an array of substantially parallel germicidal beams aligned along the straight portion of the flow path, at least one of said means for transferring being immersed in said fluid medium;

providing a secondary flow of substantially particle free fluid, said secondary flow running along or flowing across the surface of the at least one of said means for transferring which is in said fluid medium and establishing a substantially particulate free barrier environment maintaining the immersed means for transferring clean; and;

providing means for energizing of said means for killing microorganisms and energizing said means for killing microorganisms.

2. The method of claim 1, further comprising the step of: filtering said secondary flow.

3. The method of claim 2 wherein the step of: providing a secondary flow includes the step of supplying said secondary flow of substantially particulate free fluid from said primary flow of the fluid medium, the secondary fluid being the same fluid as the primary fluid.

4. The method of claim 1 wherein the step of energizing said means for killing microorganisms includes and is accomplished by energizing one or more arcs of ultraviolet lamps which emit ultraviolet germicidal beams.

5. The method of claim 1 further comprising the step of: passing said primary flow along a path aligned with said array of substantially parallel germicidal beams, said path being of sufficient length to allow said array of parallel germicidal beams to kill microorganisms.

6. The method of claim 4 further comprising the step of: providing a substantially parabolic reflector around each said ultraviolet lamp.

7. The method of claim 5 wherein the means for transferring and orienting includes reflectors, each said reflector having an aperture for accepting at least a portion of said secondary flow of substantially particle free fluid medium; and passing said portion of said secondary flow of substantially particle free fluid medium through each said reflector.

8. A method of claim 1 wherein one of said means for transferring is a fluid impenetrable transmissible wall which imperviously separates said primary flow from said means for transferring and orienting and said means for energizing.

9. An apparatus for killing microorganisms in a primary flow of a fluid medium using a germicidal beams as a means for killing microorganisms in a straight portion of the flow of the fluid medium containing particles and microorganisms, the apparatus comprising:

a means for passing a primary flow of a fluid medium containing particles and microorganisms, the means for passing having a straight prime conduit, a means for killing microorganisms, said means for killing being an emission of germicidal beams; a plurality of means for transferring the emission of germicidal beams, the plurality of means for transferring including at least one means for transferring and orienting the emission of germicidal beams into an array of substantially parallel beams aligned along the flow path of the fluid medium in the straight prime conduit; at least one of said means for transferring being immersed in said fluid medium;

a means of energizing said means for killing microorganisms;

a means for passing a secondary flow of a substantially particle free portion of said fluid medium; wherein said means for passing causes said secondary flow to run along or flow across the surface of said means for transferring which is immersed in said primary flow to establish a substantially particulate free barrier environment maintaining clean said means for transferring.

10. The apparatus for killing microorganisms in a fluid medium of claim 9 wherein said means for passing said secondary flow of said fluid medium has a filter, said filter being sufficient to remove particles from said secondary flow.

11. The apparatus for killing microorganisms of claim 9 wherein said means for energizing are one or more arcs of ultraviolet lamps and said germicidal beams are beams of ultraviolet radiation.

12. The apparatus of claim 11 wherein said means for transferring and orienting orients the emission of the ultraviolet beams into a substantially parallel array of beams; said means for transferring and orienting said ultraviolet beams being a substantially parabolic reflector.

13. The apparatus of claim 12 wherein the means for passing said primary flow of said fluid medium in a straight line direction has the straight prime conduit being aligned with said array of substantially parallel ultraviolet beams, said path being of sufficient length to allow said array of beams of ultraviolet radiation to kill microorganisms.

14. The apparatus of claim 13 wherein said means for passing said primary flow includes the straight prime conduit, said means for transferring and orienting the emission of germicidal beams is situated at the end of said straight prime conduit and is faced towards the straight prime conduit so that the array of germicidal beams are directed down the length of the straight prime conduit.

15. The apparatus of claim 13, wherein said means for passing said secondary flow have a secondary conduit, the inlet of said secondary conduit connected to said prime conduit and open for entrance of said primary flow.

16. The apparatus of claim 14 wherein said means for transferring and orienting is open to the straight prime conduit and said means for transferring and orienting is open for passing said secondary flow of the substantially particle free portion of the fluid medium.

17. The apparatus of claim 12, wherein said substantially parabolic reflector has an aperture open to said secondary flow.

18. A method for killing microorganisms in a flowing air medium using germicidal beams as a means for killing the microorganisms in a straight portion of the flow path, the method comprising of steps of:

providing a primary flow of air containing particles and microorganisms;

providing a means for killing microorganisms, the means being an emission of germicidal beams, said means being immersed in said air containing particles and microorganisms along a straight portion of the flow path;

providing a plurality of means for a transferring the emission of the germicidal beams, at least one of said means for transferring being a means for transferring and orienting of said emission of the germicidal beams, said means for transferring and orienting orients the emission in an array of substantially parallel germicidal beams aligned along the straight portion of flow path, at least one of said means for transferring being immersed in said air;

providing a secondary flow of substantially particle free air, said secondary flow is running along or flowing across the surface of the at least one of said means for transferring which is immersed in said air and establishing a substantially particulate free barrier environment maintaining the means for transferring clean;

providing means for energizing said means for killing microorganisms and energizing said means for killing microorganisms.

* * * * *